(12) United States Patent
Kamal et al.

(10) Patent No.: US 11,426,122 B2
(45) Date of Patent: Aug. 30, 2022

(54) GLOVE

(71) Applicant: The Aga Khan University, Karachi (PK)

(72) Inventors: Ayeesha Kamran Kamal, Karachi (PK); Saleem Sayani, Wynnewood, PA (US); Hafiz Imtiaz Ahmed, Karachi (PK); Hafsa Talat, Karachi (PK); Muhammad Abdul Muqeet, Karachi (PK); Ambreen Amir Ali, Karachi (PK); Shariq Ramzan Ali Khoja, Oakville, CA (US); Saad Abdullah, Karachi (PK)

(73) Assignee: The Aga Khan University, Karachi (PK)

( * ) Notice: Subject to any disclaimer, the term of this patent is extended or adjusted under 35 U.S.C. 154(b) by 35 days.

(21) Appl. No.: 16/172,173

(22) Filed: Oct. 26, 2018

(65) Prior Publication Data
US 2020/0085373 A1 Mar. 19, 2020

(30) Foreign Application Priority Data
Sep. 13, 2018 (PK) .................................... 634/2018

(51) Int. Cl.
*A61B 5/00* (2006.01)
*A61B 5/0205* (2006.01)
(Continued)

(52) U.S. Cl.
CPC .......... *A61B 5/6806* (2013.01); *A61B 5/0002* (2013.01); *A61B 5/0205* (2013.01); *A61B 5/7278* (2013.01); *A61B 5/743* (2013.01); *A61B 5/7435* (2013.01); *A61B 5/7475* (2013.01); *A61B 5/02241* (2013.01); *A61B 5/14532* (2013.01);
(Continued)

(58) Field of Classification Search
CPC ..... A61B 5/6806; A61B 5/743; A61B 5/7475; A61B 5/7278; A61B 5/0002; A61B 5/7435; A61B 5/0205; A61B 5/14551; A61B 5/0464; A61B 5/14532; A61B 5/02241;
(Continued)

(56) References Cited

U.S. PATENT DOCUMENTS 8,764,651 B2 7/2014 Tran
9,320,441 B1 4/2016 Hays
(Continued)

FOREIGN PATENT DOCUMENTS

WO WO-2015/127059 A2 8/2015

*Primary Examiner* — Gary Jackson
*Assistant Examiner* — Sebastian X Lukjan
(74) *Attorney, Agent, or Firm* — Fish & Richardson P.C.

(57) ABSTRACT

A glove is described to simultaneously, non-invasively, and continuously, over a period of time, monitor physiological parameters (e.g., blood pressure, blood glucose, oxygen saturation level, electrical activity of the heart, and/or heart rate) of a patient. A computing server that is either communicatively coupled to the glove or is a part of the glove uses the monitored physiological parameters to determine whether the patient has a physiological condition (e.g., hypotension, hypertension, hypoglycemia, hyperglycemia, hypoxia, hyperoxia, arrhythmia, a strong form of tachycardia, a mild form of tachycardia, and/or bradycardia). Related apparatuses, systems, methods, techniques and articles are also described.

19 Claims, 16 Drawing Sheets

(51) Int. Cl.
    *A61B 5/022*     (2006.01)
    *A61B 5/145*     (2006.01)
    *A61B 5/1455*    (2006.01)
    *A61B 5/30*      (2021.01)
    *A61B 5/363*     (2021.01)

(52) U.S. Cl.
    CPC .............. *A61B 5/14551* (2013.01); *A61B 5/30* (2021.01); *A61B 5/363* (2021.01)

(58) Field of Classification Search
    CPC ......... A61B 5/0428; A61B 5/30; A61B 5/363; A61B 5/145; A61B 5/332
    See application file for complete search history.

(56) References Cited

U.S. PATENT DOCUMENTS

| | | | |
|---|---|---|---|
| 2006/0074324 A1* | 4/2006 | Wu | A61B 5/021 600/490 |
| 2007/0071643 A1 | 3/2007 | Hall et al. | |
| 2008/0001735 A1* | 1/2008 | Tran | G08B 21/02 340/539.22 |
| 2008/0219319 A1 | 9/2008 | Buckalew | |
| 2010/0160746 A1 | 6/2010 | Venkatraman et al. | |
| 2011/0224530 A1* | 9/2011 | David | A61B 5/0006 600/388 |
| 2011/0245628 A1* | 10/2011 | Baker, Jr. | A61B 5/02416 600/301 |
| 2015/0173631 A1* | 6/2015 | Richards | A61B 5/02427 600/479 |
| 2015/0366518 A1* | 12/2015 | Sampson | A61B 5/0261 600/301 |
| 2016/0045527 A1* | 2/2016 | Bowden | A61K 9/0053 514/23 |
| 2016/0287148 A1* | 10/2016 | Pizer | A61B 5/14546 |
| 2016/0374567 A1* | 12/2016 | Breslow | A61B 5/4809 600/301 |
| 2017/0079533 A1* | 3/2017 | Robinson | A61B 5/0075 |
| 2017/0235332 A1* | 8/2017 | von Badinski | G04G 21/02 361/679.03 |
| 2017/0340217 A1* | 11/2017 | Hsu | A61B 5/0261 |

\* cited by examiner

FIG. 12

GLOVE

RELATED APPLICATION

This disclosure claims priority to Pakistan Patent Application No. 634/2018, filed on Sep. 13, 2018, and entitled "Glove", the entire contents of which are hereby fully incorporated by reference.

TECHNICAL FIELD

The subject matter described herein relates to a glove used to simultaneously, non-invasively, and continuously, over a period of time, monitor physiological parameters (e.g., blood pressure, blood glucose, oxygen saturation level, electrical activity of the heart, and/or heart rate) of a patient, and a computing server that is either communicatively coupled to the glove or is a part of the glove and uses the monitored physiological parameters to determine whether the patient has one or more physiological conditions (e.g., hypotension, hypertension, hypoglycemia, hyperglycemia, hypoxia, hyperoxia, arrhythmia, a strong form of tachycardia, a mild form of tachycardia, and/or bradycardia).

BACKGROUND

Blood pressure, blood glucose, oxygen saturation level, electrical activity of the heart, and heart rate play a vital role in fundamental processes of the human body. It is accordingly important to maintain their optimum levels to avoid diseases or bodily disorders. These physiological parameters are traditionally monitored separately using several diagnostic devices, such as a glucometer to check glucose, a pulse oximeter to measure oxygen saturation level in blood, a sphygmomanometer to measure blood pressure, an electrocardiogram to check the electrical activity of the heart, and the like. However, these devices cannot be used simultaneously because they have different configurations and requirements, and application programming interfaces (APIs) that may enable communication between such devices do not exist. Moreover, these devices are not configured to be used simultaneously, either spatially or technically. Additionally, such conventional devices monitor physiological parameters (e.g., blood glucose) at a single time instance rather than continuously over a period of time, and therefore are unable to accurately predict likelihood of clinical conditions—e.g., hypoglycemia or hyperglycemia—for which diagnosis is either required or encouraged at different or continuous points in time. There, accordingly, exists a need for a medical device that can simultaneously monitor different physiological parameters (e.g., blood pressure, blood glucose, oxygen saturation level, and/or electrical activity of the heart) in a non-invasive manner continuously over a period of time. There further exists a need for a system that can generate a diagnosis of a physiological condition based on such monitoring of physiological parameters.

SUMMARY

The current subject matter relates to a medical device (e.g., a glove) that can simultaneously measure different physiological parameters (e.g., blood pressure, blood glucose, oxygen saturation level, electrical activity of the heart, and/or heart rate) of a patient in a non-invasive manner continuously over a period of time, and a computing server that is either communicatively coupled to the glove or is a part of the glove and uses the monitored physiological parameters to determine whether the patient has a physiological condition (e.g., hypotension, hypertension, hypoglycemia, hyperglycemia, hypoxia, hyperoxia, arrhythmia, high, a strong form of tachycardia, a mild form of tachycardia, and/or bradycardia).

In one aspect, a glove is described that can include an infrared sensor, a plurality of electrocardiograph connectors, and/or a cuff. The infrared sensor can be configured to be placed around the index finger of a patient. The infrared sensor can be configured to monitor blood glucose of the patient. The plurality of electrocardiograph connectors can be configured to monitor electrical activity of a heart of the patient when the electrocardiograph is placed close to the heart of the patient. The cuff can be configured to use a pressure sensor monitor measure a systolic blood pressure and a diastolic blood pressure of the patient. The monitoring of the blood glucose, the electrical activity, the systolic blood pressure and the diastolic blood pressure can occur simultaneously.

In some variations, one or more of the following can be implemented either individually or in any feasible combination. The blood glucose, the electrical activity, the systolic blood pressure and the diastolic blood pressure can be monitored non-invasively. The glove can further include one or more processors that can be communicatively coupled to a computing server configured to diagnose physiological conditions based on monitored readings of the blood glucose, the electrical activity, the systolic blood pressure and the diastolic blood pressure. The one or more processors and the computing server can be communicatively coupled to a communication device that executes a first application. The first application can display the diagnosed physical conditions on a graphical user interface of the communication device. The physiological conditions can include two or more of hypotension, hypertension, hypoglycemia, hyperglycemia, hypoxia, hyperoxia, and arrhythmia. The plurality of electrocardiograph connectors can be three electrocardiograph connectors. The infrared sensor can measure the blood glucose over a period of time.

In another aspect, a system is described that includes a glove and a computing device. The glove can be configured to simultaneously and non-invasively monitor a plurality of physiological parameters of a patient. The computing device can be executing an application configured to: receive, via a first communication network, readings of the plurality of physiological parameters; apply an algorithm on the readings to generate a diagnosis of one or more physiological conditions of the patient; and display the diagnosis on a display screen of the application.

In some variations, one or more of the following can be implemented either individually or in any feasible combination. The plurality of physiological parameters can include two or more of blood pressure, blood glucose, oxygen saturation level, and electrical activity of the heart of the patient. The one or more physiological conditions can include one or more of hypotension, hypertension, hypoglycemia, hyperglycemia, hypoxia, hyperoxia, and arrhythmia. The generation of the diagnosis can include generating a PQRST complex based on the electrical activity of the heart. The generation of the diagnosis can include averaging the blood pressure over a preset period of time. The application can be further configured to communicate with a computing server via a communication network to create a database of clinical data of the patient. The database can be a part of the computing server. The computing server can be a cloud computing server.

In yet another aspect, a process is described that can include the following. A glove worn by a patient can simultaneously acquire a plurality of readings of a plurality of physiological parameters from a patient. A transmitter of the glove can transmit, via a communication network, the plurality of readings to an application executed on a computing device.

In some variations, one or more of the following can be implemented either individually or in any feasible combination. The plurality of physiological parameters can include two or more of blood pressure, blood glucose, oxygen saturation level, and heart rate. The application can display one or more physiological conditions determined based on the plurality of physiological parameters, the one or more physiological conditions comprise one or more of hypotension, hypertension, hypoglycemia, hyperglycemia, hypoxia, hyperoxia, arrhythmia, a strong form of tachycardia, a mild form of tachycardia, and bradycardia.

The subject matter described herein provides many advantages. For example, the glove described herein can provide a way for patients to have several physiological parameters—e.g., blood pressure, blood glucose, oxygen saturation level, electrical activity of the heart, and/or heart rate—monitored simultaneously, thereby avoiding the inconvenience of using multiple devices separately to measure these physiological parameters. The convenience offered by the glove can be beneficial for everyone, and especially for a patient that is bed-ridden, has difficulty or inconvenience in moving, is hospitalized, is disabled, or the like. The computing server described herein can communicate with the glove to promptly—i.e., in real-time—and accurately detect physiological conditions (e.g., hypotension, hypertension, hypoglycemia, hyperglycemia, hypoxia, hyperoxia, arrhythmia, a strong form of tachycardia, a mild form of tachycardia, and/or bradycardia), and can notify a patient upon such detection in real-time. Such notification can help patients avoid such physiological conditions, thereby facilitating good health and longevity.

The details of one or more variations of the subject matter described herein are set forth in the accompanying drawings and the description below. Other features and advantages of the subject matter described herein will be apparent from the description, the drawings, and the claims.

BRIEF DESCRIPTION OF DRAWINGS

FIG. 12 illustrates a display screen of a clinician-application that is hosted by the computing server and is executed on a clinician's computing device communicatively coupled to the computing server, in accordance with some implementations of the current subject matter;

Like reference symbols in the various drawings indicate like elements.

DETAILED DESCRIPTION

Figure 1:
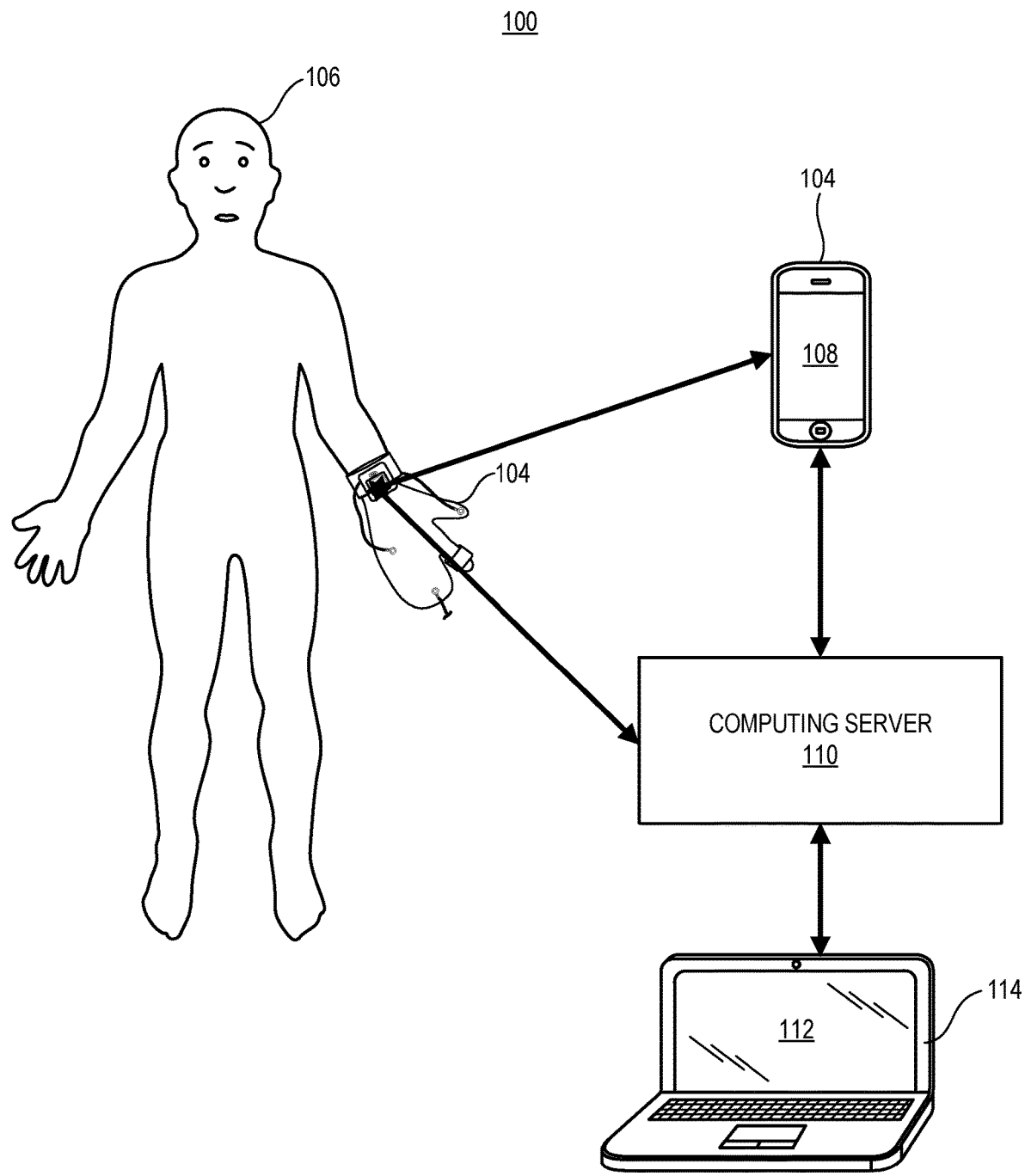
FIG. 1 illustrates a computing landscape in which a glove configured to monitor physiological parameters of a patient is used in conjunction with a computing device that executes a patient-application to diagnose possible physiological conditions of the patient based on the monitored physiological parameters, in accordance with some implementations of the current subject matter.

FIG. 1 illustrates a computing landscape 100 in which the glove 102 can be used in conjunction with a computing device 104. The computing device 103 can execute a patient-application 108 that can facilitate the activation and deactivation of the glove 102 to monitor physiological parameters (e.g., blood pressure, blood glucose, oxygen saturation level, electrical activity of the heart, and/or heart rate) of a patient 106. The patient-application 108 can be hosted by a computing server 110. While the computing server 110 is shown as being communicatively coupled to the glove 102, in an alternate implementation the computing server 110 can be a part of (i.e., within) the glove 102. Using the physiological parameters monitored by the glove 102, it can be diagnosed whether the patient 106 has a physiological condition, such as hypotension, hypertension, hypoglycemia, hyperglycemia, hypoxia, hyperoxia, arrhythmia, a strong form of tachycardia, a mild form of tachycardia, and/or bradycardia. Such diagnosis can be made in different manners in different implementations.

In a first implementation, the patient-application 108 can generate the diagnosis using the processing power of the computing device 104. In a second implementation, the computing server 110, instead of the computing device 104, can generate the diagnosis. For such first implementation and second implementation, some examples of the algorithms for diagnosing/identifying one of more physiological conditions of the patient 106 are described in greater detail below by FIGS. 14-16. These algorithms differentiate between physiological responses and pathological responses to continuous changes in physiological parameters of the patient 106. Also, these algorithms take into account medically important risk factors such as family history of cardiac disease, presence or absence of diabetes mellitus, and/or the like. In a third implementation, the patient-application 108 can communicate with a clinician-application 112 executed on a computing device 114 via the computing server 110. In that third implementation, a clinician can review the monitored physiological parameters displayed—either in real-time or later in time, depending on the physiological urgency, suspected physiological condition, availability of the clinician, and/or the like—on the clinician-application 112 and can input a diagnosis on the clinician-application 112, which can then transmit the diagnosis to the patient-application 108 for display thereon.

The glove 102 is described in further detail below by FIGS. 2 and 3. The glove 102 can be used and may be recommended where the patient 106 has had or is at risk for abnormal values of physiological parameters, such as blood pressure, blood glucose, oxygen saturation level, and/or electrical activity of the heart. Such a patient often exhibits symptoms for these physiological parameters. In one implementation, the patient-application 108 can transmit the diagnosis of to the glove 102, which can then display the diagnosis.

Some symptoms for low blood pressure (i.e., hypotension) include fatigue, lightheadedness, dizziness, nausea, clammy skin, depression, loss of consciousness, and/or blurry vision. A patient with high blood pressure (e.g., hypertension) may not exhibit any symptoms. Some early symptoms for low blood glucose (i.e., hypoglycemia) include confusion, dizziness, feeling shaky, hunger, headaches, irritability, pounding heart, racing pulse, pale skin, sweating, trembling, weakness, and/or anxiety. Some symptoms for high blood glucose (i.e., hyperglycemia) include increased thirst, headaches, trouble concentrating, blurred vision, frequent peeing, fatigue, and/or weight loss. Some symptoms for low oxygen levels (i.e., hypoxia or hypoxemia) include changes in the color of skin (ranging from blue to cherry red), confusion, cough, fast heart rate, rapid breathing, shortness of breath, sweating, and/or wheezing.

Some symptoms for high oxygen levels (i.e., hyperoxia) include irritation or congestion in the lungs. Symptoms of abnormal electrical activity of heart (i.e., arrhythmia) include a fluttering in chest, a racing heartbeat (i.e., tachycardia), a slow heartbeat (i.e., bradycardia), chest pain, shortness of breath, lightheadedness or dizziness, sweating, and/or fainting (i.e., syncope) or near fainting. The glove 102 can benefit an individual exhibiting one or more of these symptoms.

The computing device 104 can be a mobile phone. Although a mobile phone is described, in alternate implementations, the computing device 104 can be a tablet computer, a phablet computer, a laptop, a desktop computer, any other computing device, or any combination thereof.

The patient 106 can be any individual. The patient may exhibit one or more of the symptoms discussed above for one or more of the above-mentioned physiological conditions.

The patient-application 108 can be a software application executed on the computing device 104, which can have an iPhone operating system (IOS), ANDROID, or any other operating system. One example of the patient-application 108 is described in further detail below by FIGS. 5-11. The patient-application 108 can be operated by the patient 106 or any other user authorized by the patient 106, such as a caretaker, a clinician, and/or the like.

The computing server 110 can be a device or a computer program that can provide functionality for the glove 102 and/or the computing device 104, which can be referred to as clients of the computing server 110. The computing server 110 can be a cloud computing server, as explained below by FIG. 4. In an alternate implementation, the computing server 110 can be a cluster of computers. In another implementation, the computing server 110 can be one or more of: a desktop computer, a laptop computer, a tablet computer, a phablet computer, a cellular/smart phone, and any other suitable computing device. The computing server 110 can be communicatively coupled with each of the glove 102, the computing device 104, and the computing device 114 via a communication network, such as one or more of: local area network, internet, wide area network, metropolitan area network, BLUETOOTH network, infrared network, wired network, and any other communication network.

The clinician-application 112 can be a software application executed on the computing device 114, which can have an iPhone operating system (IOS), ANDROID, or any other operating system. One example of the clinician-application 112 is described in further detail below by FIG. 12.

The computing device 114 can be one or more of: a desktop computer, a laptop computer, a tablet computer, a phablet computer, a cellular/smart phone, and any other suitable computing device.

As noted above, FIGS. 14-16 describe below examples of the algorithms for diagnosing/identifying one of more physiological conditions of the patient 106. These algorithms differentiate between physiological responses and pathological responses to continuous changes in physiological parameters of the patient 106.

Figure 2:
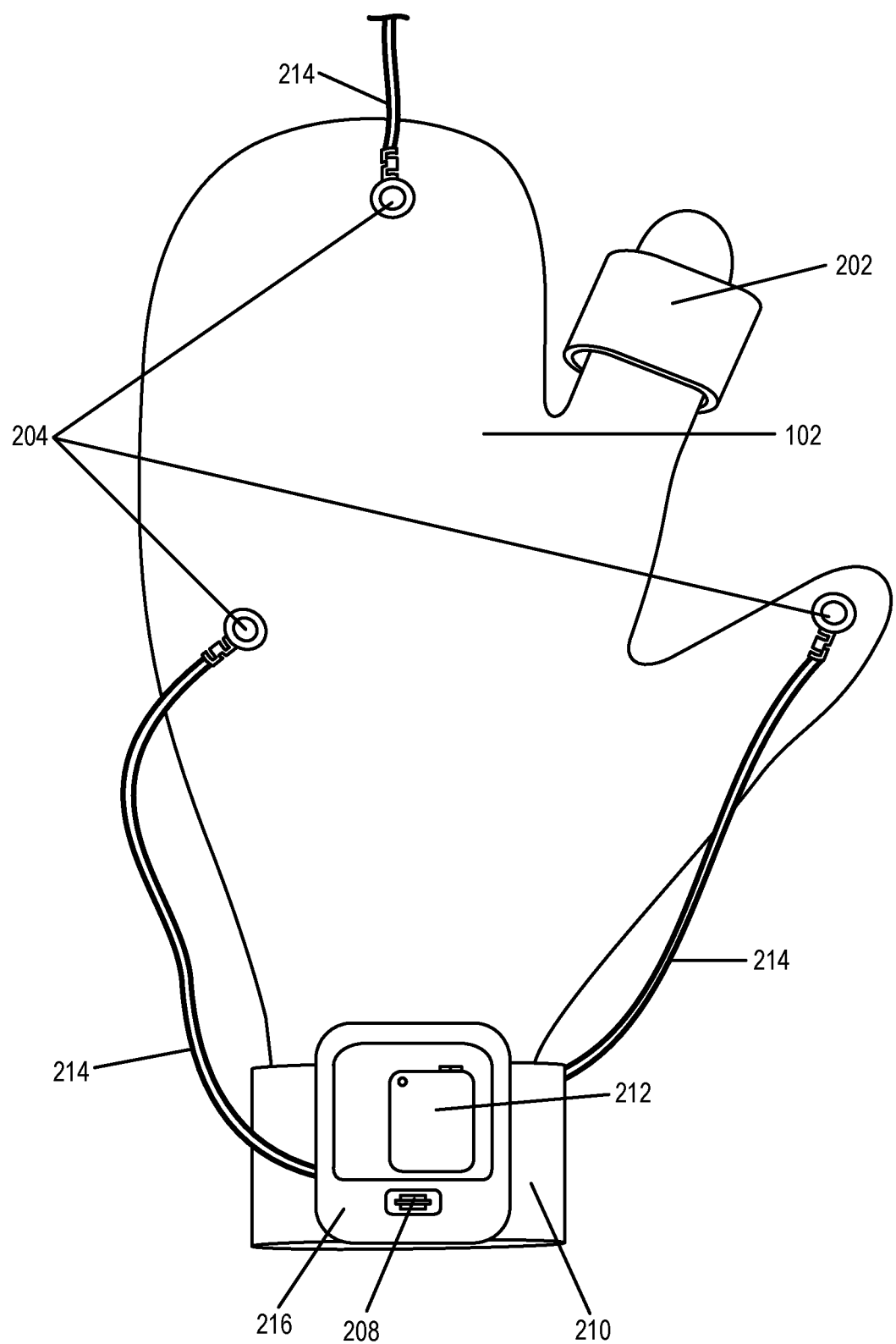
FIG. 2 illustrates a front view of the glove, in accordance with some implementations of the current subject matter.

FIG. 2 illustrates a front view of the glove 102. The glove 102 includes a sensor 202, electrocardiography (ECG) lead connectors 204, device case 206, a start/stop button 208 on the device case 206, a blood pressure measuring cuff 210, a display device 212 for displaying the readings of monitored physiological parameters. The glove can further include ECG lead wires 214 connected with the ECG lead connectors 204 (as shown here) and the device case 206 (as shown in FIG. 3).

The sensor 202 can be an infrared sensor that takes a non-invasive blood glucose reading. The sensor 202 is configured to be placed around the index finger of a patient rather than other fingers because the index finger is the most likely to have the most amount of blood for most patients, as per the following. The index finger is serviced by more number of arteries—deep palmer arch, superficial palmar arch, and proper digital arteries to the fingers, and radial artery of the index finger—than number of arteries servicing each of the other fingers. The infrared sensor can advantageously offer the benefits of sensitivity, selectivity, low cost, and portability.

While three ECG lead connectors 204 are described, in alternate implementations the glove 102 can have any other number of ECG lead connectors 204, such as two, four, five, six, seven, eight, nine, ten, eleven, twelve, thirteen, or so on.

The device case 206 can include a circuit board having electrical circuitry, which can include: a microcontroller including one or more processors that perform the operations of the device case 206; one or more storage devices—which can store data associated with the glove 102 (e.g., readings of physiological parameters measured by the glove)—including main memory, cache memory, and/or disk storage; one or more batteries (e.g., rechargeable batteries) that power the device case 206; one or more pressure sensors that sense pressure in the hand of the patient 106; one or more air pumps that can produce air to the hand of the patient 106; an electromechanical device (e.g., a mini solenoid valve) that uses electrical circuitry to produce magnetic field that facilitates the functioning of the one or more air pumps; and communication apparatus that can enable communication between the device case 206 (and thus the glove 102) and the computing device 104 that executes the patient-application 108. In another implementation, the electrical circuitry of the device case 206 can further (or alternately where any other functionality is not affected adversely) include any other electrical component that can facilitate any functionality of the glove 102. The electrical circuitry within the device case 206 can be water proof and/or washable.

The start/stop button 208 can be used to start or stop the monitoring of the physiological parameters using the glove 102. The start/stop button 208 can be a mechanical button that needs to be physically pressed by a user (e.g., patient 106). In some implementations, the activation/deactivation of the start/stop button 208 can be controlled remotely via the patient-application 108 and/or the clinician-application 112.

The blood pressure measuring cuff 210 can be operable and/or physically coupled to the device case 206. The blood pressure measuring cuff can interact with the one or more pressure sensors, the one or more air pumps, and the mini solenoid valve within the device case 206 to measure a systolic blood pressure and a diastolic blood pressure of the patient 106.

The display device 212 can be a light emitting diode (LED) monitor, a cathode ray tube (CRT) device, a liquid crystal display (LCD) monitor, an electroluminescent display (ELD) device, a plasma display panel (PDP), an organic light-emitting diode display (OLED) device, or any other display device.

The ECG lead wires 214 can connect the ECG lead connectors 204 with the electrical circuitry within the device case 206. For measurement of bodily electrical activity using the glove 102, the glove 102, when operational, needs to be placed on the chest of the patient 106 with the side of the glove 102 that has the ECG lead connectors 204 facing the chest. Further, in an alternate implementation, the ECG lead wires 214 may be replaced by wireless connection between the ECG lead connectors 204 with the electrical circuitry within the device case 206 via a wireless communication network, such as a BLUETOOTH network. Although a BLUETOOTH network is described here, in alternate implementations any other suitable wireless network can be used.

When the start/stop button 208 is pressed (e.g., by the patient 106 or any other individual permitted by the patient 106), the one or more processors within the electrical circuitry of the device case 206 can render a display of an initializing message on the display device 212. After the display device 212 displays the initialization message, the sensor (e.g., infrared sensor) 202 can take a reading of a physiological parameter (e.g., blood glucose) and transmit the reading to the one or more processors via a communication network (e.g., infrared network). In some implementations, the display device 212 can display the reading. The display device 212 can display an error message if a technical error occurs during the monitoring of the physiological parameters. The error message can include a suggestion for a corrective action to remedy the error. For example, the error message can suggest charging a battery of the glove 102, placing the sensor at a particular position, and/or the like. The ECG lead connectors 103 can acquire reading of another physiological parameter (e.g., the electrical activity of the body of the patient 106) from the chest of the patient, and transmit the reading to the one or more processors through the ECG lead wires 214. The one or more processors can transmit the readings of the physiological parameters to the patient-application 108 and/or the computing server 110 for diagnosis based on the readings.

The glove 102 can be made of a washable fabric that can be easy-to-use and comfortable to wear. In some implementations, the glove 102 can be flexible and/or adjustable, by flexing, to the physique of the hand of each patient 106. The adjustment to the size of the hand of each patient 106 can advantageously prevent the glove 102 from falling off easily from the hand. In one implementation, the fabric of the glove 102 can be woolen. Although a woolen fabric is described, in other implementations the glove can be alternately or additionally made of any other fabric may be used such as cotton, silk, polyester, linen, denim, shatung, damask, jute, satin, hemp, velvet, crepe, corduroy, canvas, any other one or more fabrics, and/or any combination thereof.

Figure 3:
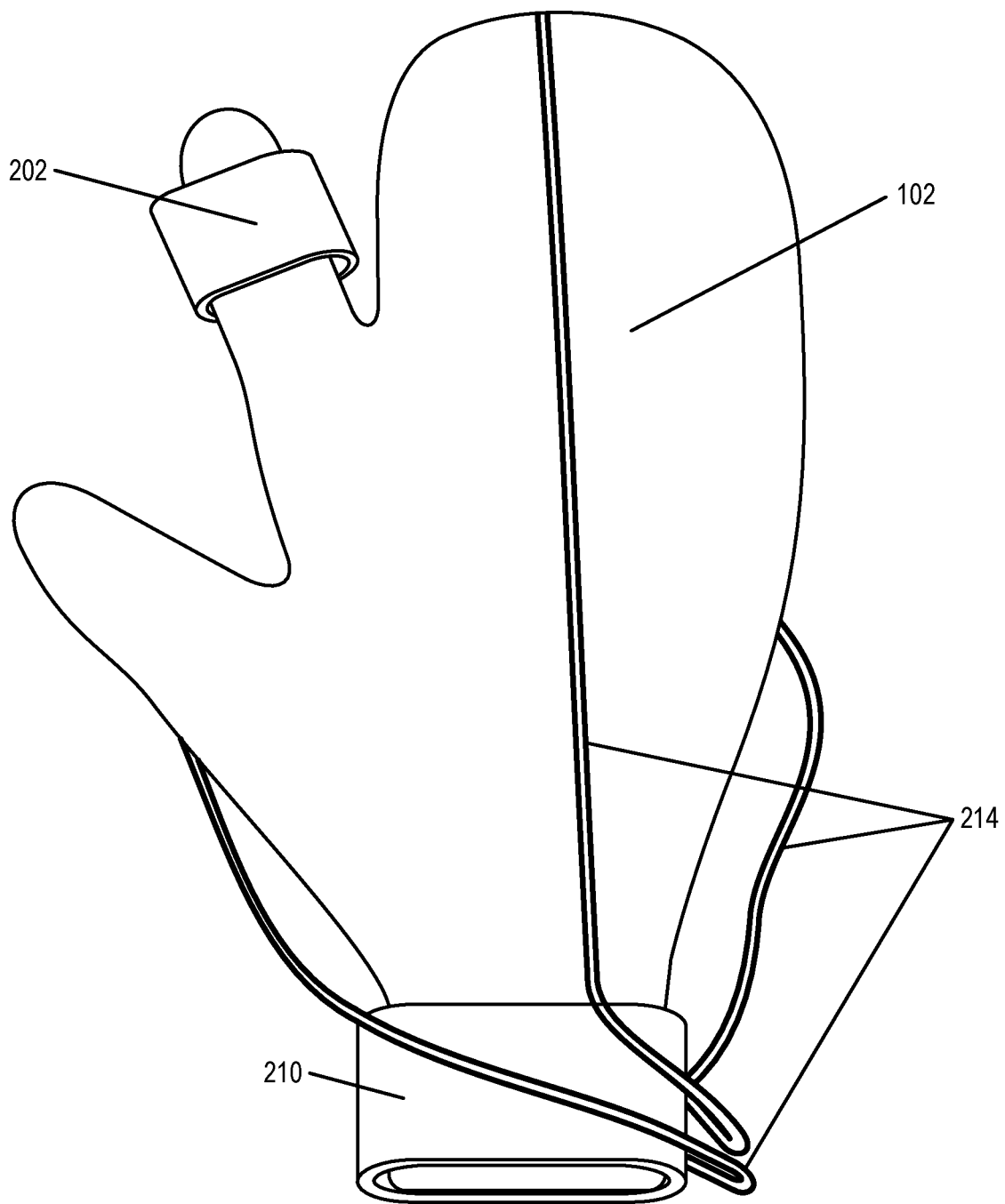
FIG. 3 illustrates a back view of the glove, in accordance with some implementations of the current subject matter.

FIG. 3 illustrates a back view of the glove 102.

Figure 4:
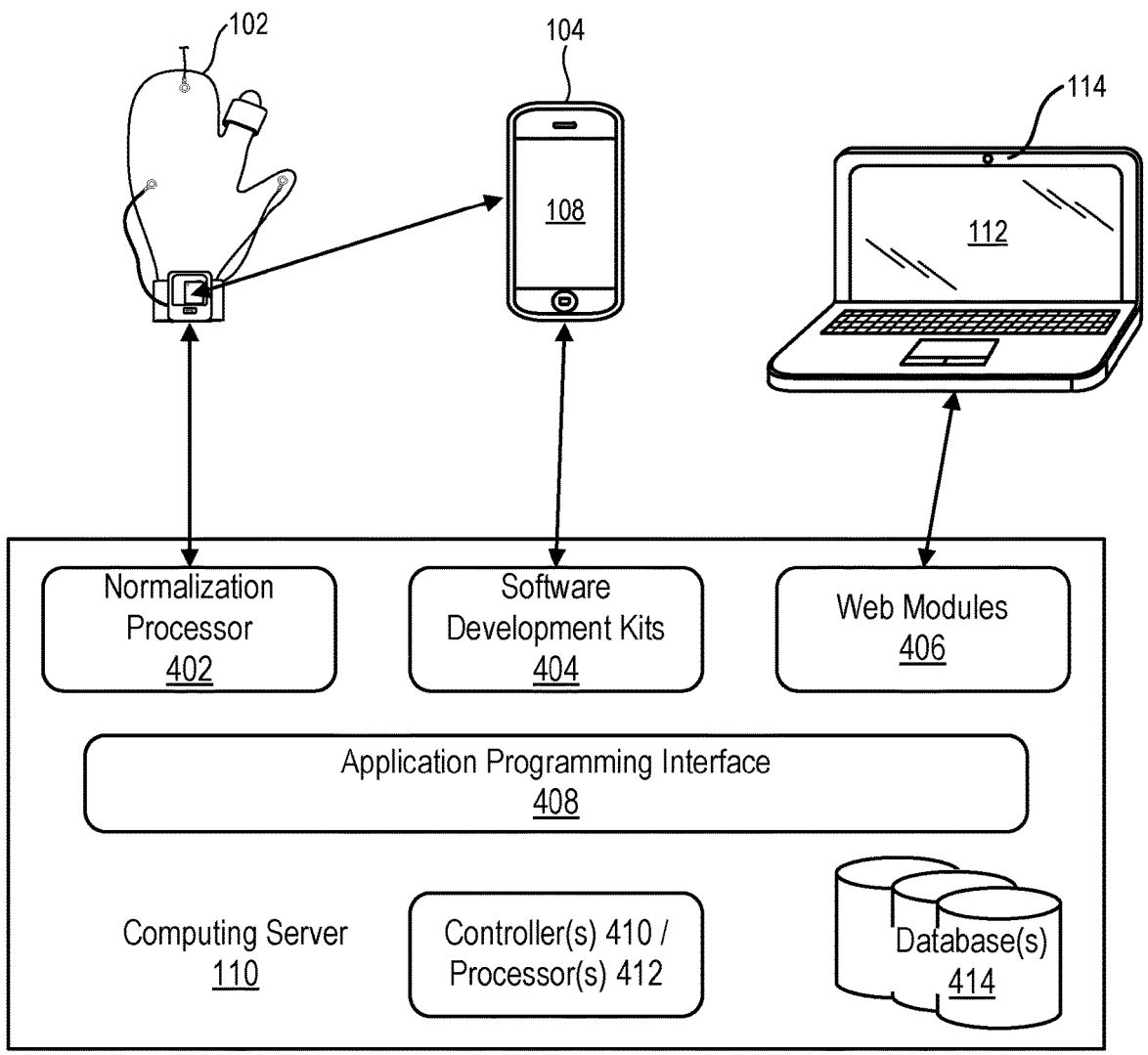
FIG. 4 illustrates one example of a computing server that hosts the patient-application executed on the computing device, in accordance with some implementations of the current subject matter.

FIG. 4 illustrates one example of the computing server 110 within the computing landscape 100. In this example, the computing server 110 is a cloud computing server. The cloud computing server 110 can include a normalization processor 402, one or more software development kits (SDKs) 404, one or more web modules 406, an application programming interface (API) 408, one or more controllers 410 including one or more processors 412, and one or more databases 414 connected to the one or more controllers 410.

The normalization processor 402 can be configured to communicate with the glove 102 via a first communication network. The one or more SDKs 404 are configured to communicate, via a second communication network, with the computing device 104 and the patient-application 108 executed thereon. The one or more web modules 406 can be configured to communicate, via a third communication network, with the computing device 114, and the clinician-application 112 executed thereon, when the computing device 114 is a laptop or a desktop computer. Each of the first communication network, the second communication network, and the third communication network can be one or more of: local area network, internet, wide area network, metropolitan area network, BLUETOOTH network, infrared network, wired network, and any other communication network. In one implementation, the first communication network, the second communication network, and the third communication network may be the same network. In another implementation, the first communication network, the second communication network, and the third communication network may be different networks. In the alternate implementation where the computing device 104 is a laptop or a desktop computer, the computing device 114 can communicate with the web modules 406. When the computing device 114 is a phone, a tablet computer or a phablet computer, the computing device 114 can communicate with the SDK 404 in that case.

The API 408 can be a set of subroutine definitions, protocols, and/or tools that define method of communication between the patient-application 108 and the computing server 110 and between the client-application 112 and the computing server 110. The API 408 can ensure, for example, that the data from the at least one of the normalization processor 402, the one or more SDKs 404, and the one or more web modules 406 can be read by the one or more controllers 410 and the one or more processors 412.

Each database 414 can be a cloud database, which can advantageously permit an easy scalability of the database 414 when required (e.g., when additional data needs to be stored, which can happen, for example, when the number of patients increase beyond a threshold value). In one implementation, access to that database 414 can be provided as a service. In some implementations, the database 414 can be run on virtual machine instances. In one implementation, the database 414 can be a disk storage. In some alternate implementations, the database 414 can be a main memory (e.g., random access memory) rather than a disk storage. In those alternate implementations, access of data from the main memory can advantageously eliminate seek time when querying the data, which can can provide a faster access of data, as compared to accessing data from the disk.

The use of a cloud computing server 110 can be advantageous over a traditional server, as the cloud computing server 110 permits a quick scalability by addition of additional web services within in a few seconds. When the load on the patient-application 108 or clinician-application 112 increases, additional processors 412 or databases 414 can be added—or alternately the processing abilities of the existing processors 412 or databases 414 can be enhanced—within a few seconds. Additionally, inclusion of all of the normalization processor 402, one or more SDKs 404, one or more web modules 406, API 408, at least one data processor 412, and database 414 within the cloud computing server 110 can advantageously enable: a dynamic provisioning, monitoring and managing of the patient-application 108 and clinician-application 112; as well as a quick (e.g., within a few seconds) and easy restoring the patient-application 108 and/or the clinician-application 112 to a previous version of those applications if and when required.

Figure 5:
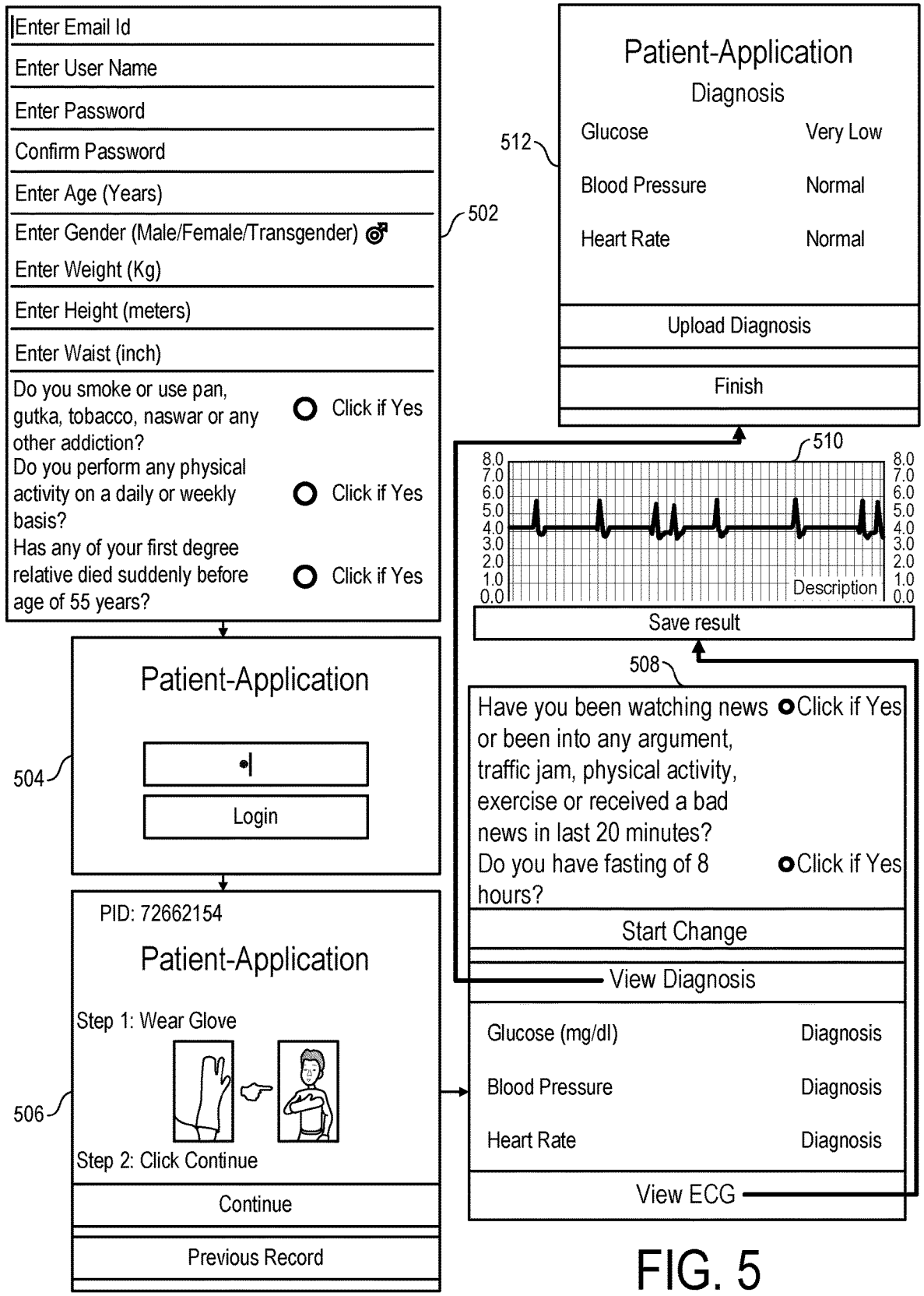
FIG. 5 illustrates the functionality of the patient-application, in accordance with some implementations of the current subject matter.

FIG. 5 illustrates the functionality of the patient-application 108. The patient-application 108 can render display screens (also referred to as graphical user interfaces) 502, 504, 506, 508, 510 and 512 on the computing device 104. The display screen 502 permits a user (e.g., the patient 106) to register to create an account. The patient-application 108 can render the display screen 504 after the user has registered and made an account on the display screen 502. The display screen 504 can enable the user to login to his or her account. The patient-application 108 can render the display screen 506 after the user has logged in to his or her account using the display screen 504. The display screen 506 can enable the user to review previous clinical data, if it has been recorded using the glove 102, and/or can provide instructions for the patient 106 regarding wearing the glove 102 for diagnosis of the physiological parameters (e.g., blood pressure, blood glucose, oxygen saturation level, and/or electrical activity of the heart) of the patient 106. Subsequently, the user can click the start/stop button 208 to begin the diagnosis of those physiological parameters. In an alternate implementation, the patient-application 108 can be operably coupled to the start/stop button 208 such that selection of an option/button on the patient-application 108 activates and deactivates the monitoring by the glove 102.

Subsequent to the diagnosis/monitoring (or alternately simultaneously during the monitoring, where the monitoring is continuous), the patient-application 108 can render the display screen 508. The display screen 508 can enable the user to view the electrical activity of the patient 106 or a diagnosis for blood glucose, blood pressure and heart rate of the patient 106. The patient-application 108 can render the display screen 510 when the user selects the option on the display screen 508 to view the ECG. The display screen 510 can display the electrical activity in the form of the PQRST complex (which can also be referred to as a PQRST wave) of the ECG of the patient 106. The patient-application 108 can render the display screen 512 when the user selects the option on the display screen 508 to view readings of the physiological parameters (e.g., blood glucose, blood pressure and heart rate). The display screen 512 can display the readings of the physiological parameters (e.g., blood glucose, blood pressure and heart rate) of the patient 106. The display screen 512 additionally can provide an option to the user to share the diagnosis over the internet either in private or public mode.

Figure 6:
FIG. 6 illustrates an expanded view of a display screen of the patient-application, as shown on a graphical user interface of the computing device, in accordance with some implementations of the current subject matter.

FIG. 6 illustrates an expanded view of the display screen 502. The display screen 502 can receive, from the user, input on software characteristics 602, biological characteristics 604, habitual characteristics 606, and familial characteristics 608. While the display screen 502 receives the readings of these characteristics, in alternate implementations the display screen 502 can receive any other similar characteristic. The patient-application 108 can receive the input for all the registration data on a single display screen, as shown, which can advantageously minimize the processing ability required to register each user and improve the speed at which the patient-application 108 runs.

Figure 7:
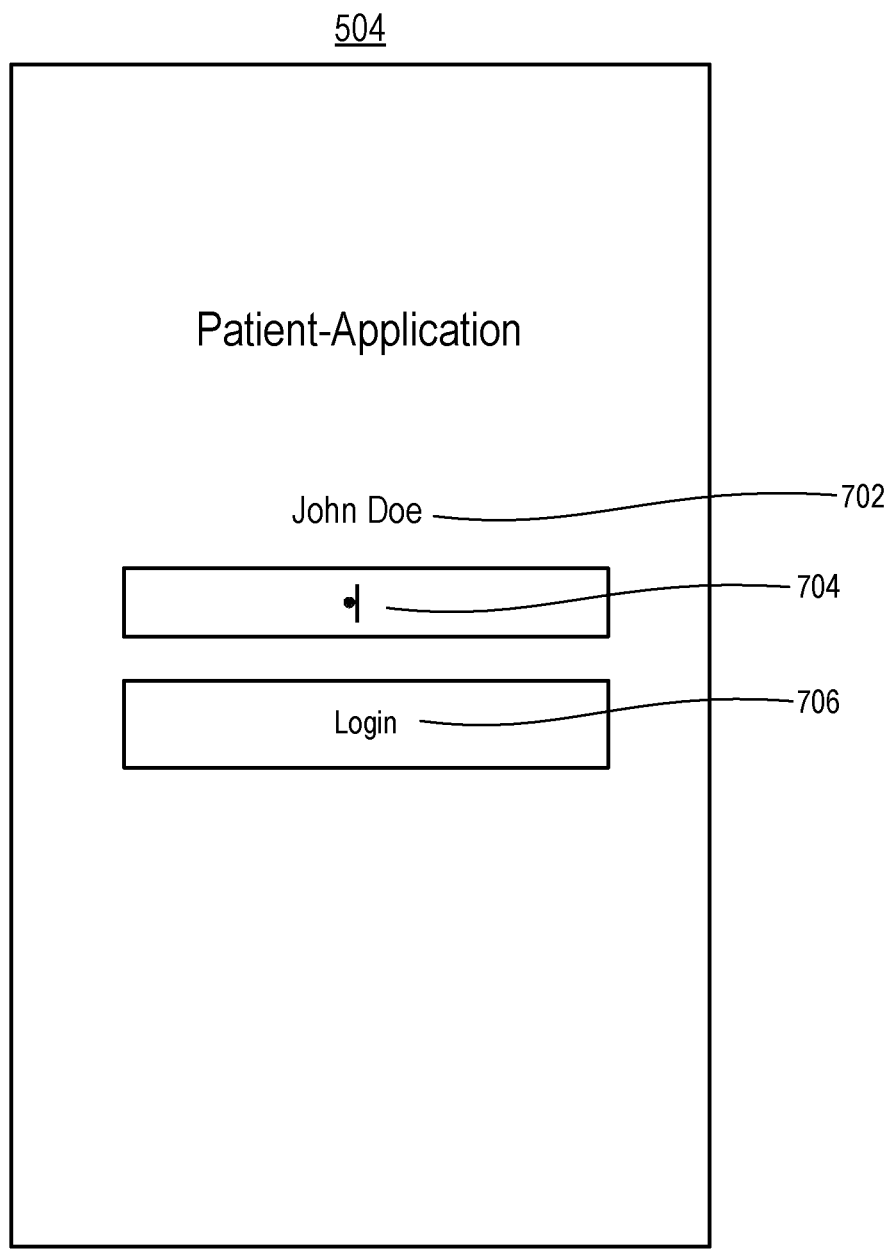
FIG. 7 illustrates an expanded view of another display screen of the patient-application, as shown on a graphical user interface of the computing device, in accordance with some implementations of the current subject matter.

FIG. 7 illustrates an expanded view of the display screen 504. The display screen 504 can display the name 702 (or alternately the username, email, or any unique identifier) provided by the user on the display screen 502, and provide space 704 for the user to input the password specified by the user on the display screen 502. The display screen 504 can include a login button 706, which, when selected by the user by clicking on it, results in the patient-application 108 permitting the user to access clinical data specific to that user.

Figure 8:
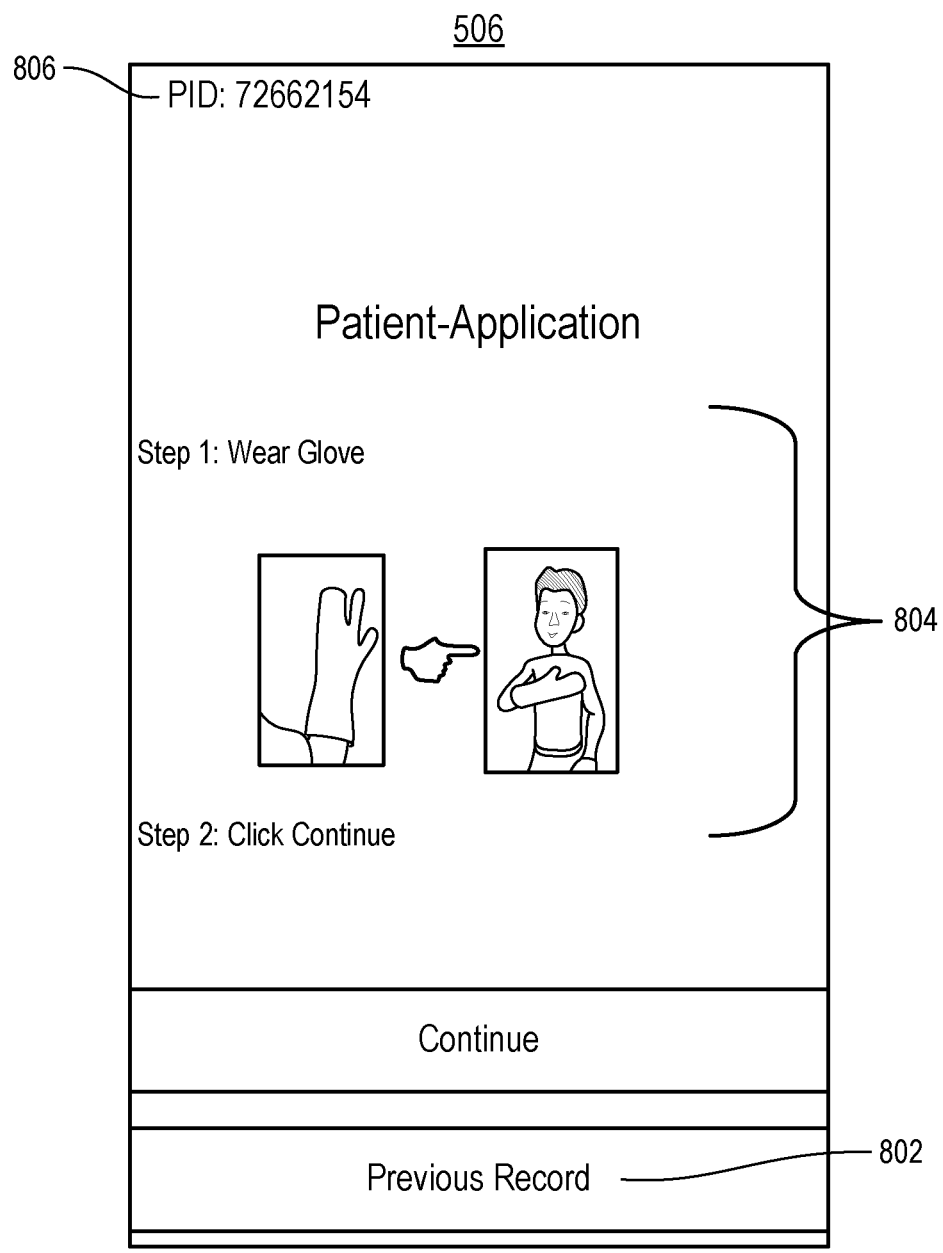
FIG. 8 illustrates an expanded view of another display screen of the patient-application, as shown on a graphical user interface of the computing device, in accordance with some implementations of the current subject matter.

FIG. 8 illustrates an expanded view of the display screen 506. The display screen 506 can enable the user to review previous clinical data, if it has been recorded using the glove 102 by clicking the button 802. The display screen 506 can provide instructions 804 for the patient 106 regarding wearing the glove 102 for diagnosis of the physiological parameters (e.g., blood pressure, blood glucose, oxygen saturation level, and/or electrical activity of the heart) of the patient 106. The display screen 506 can display a unique identifier of the patient 106. Alternately, the display screen 506 can display the name, username, email, or any other identifier of the patient 106.

Figure 9:
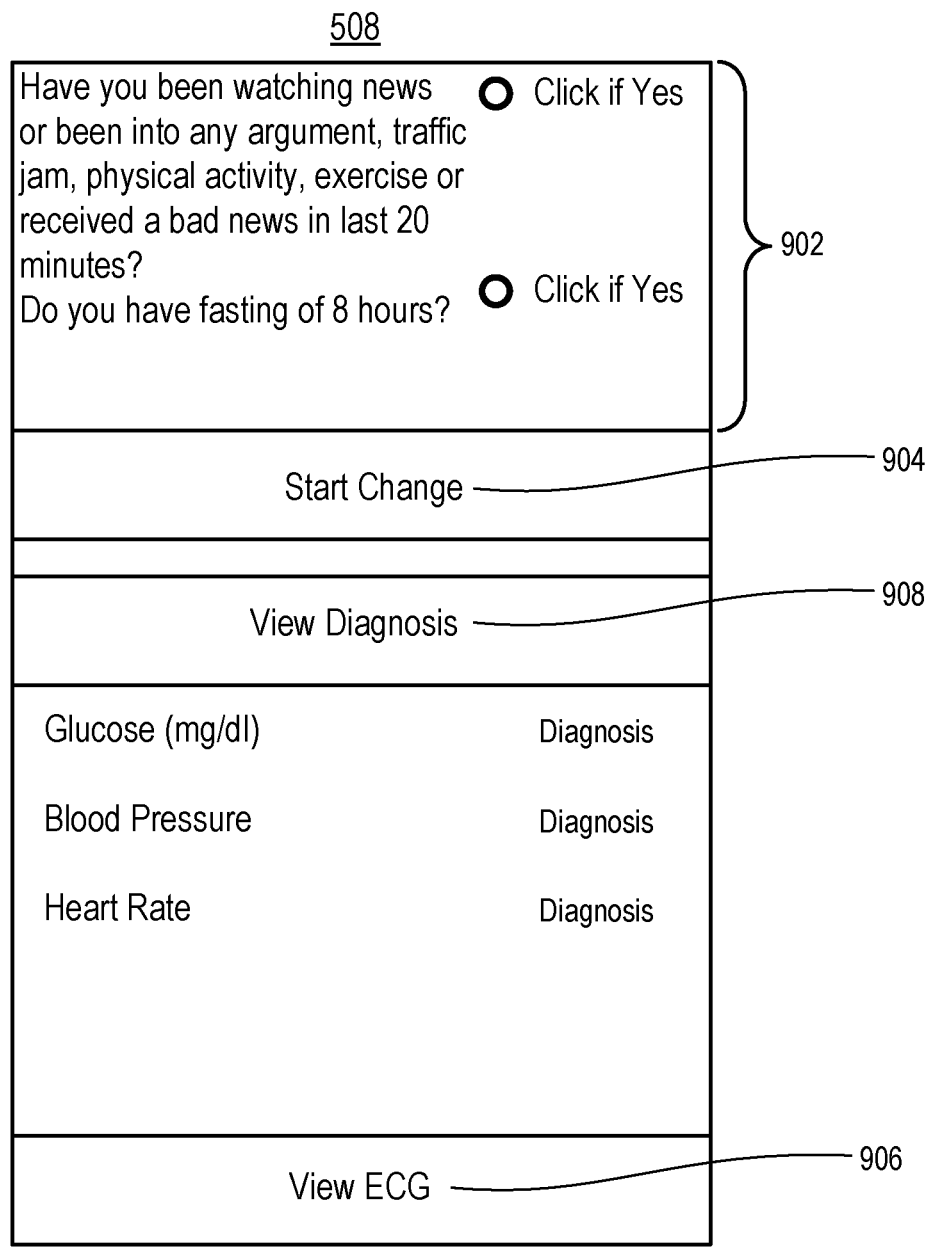
FIG. 9 illustrates an expanded view of another display screen of the patient-application, as shown on a graphical user interface of the computing device, in accordance with some implementations of the current subject matter.

FIG. 9 illustrates an expanded view of the display screen 508. The display screen 508 requests the user to input data 902 that can affect the diagnosis. The display screen 508 can provide a button 904, which, when selected by the user, directs the user to a display screen that can provide customized instructions for the user based on their activities noted within the data 902. The display screen 508 can provide a button 906, which, when selected by the user, can cause the patient-application 108 to render the display screen 510 that displays the electrical activity in the form of the PQRST complex of the ECG of the patient 106. The display screen 508 can provide a button 908, which, when selected by the user, can cause the patient-application 108 to render the display screen 512 that displays readings of the physiological parameters (e.g., blood glucose, blood pressure and heart rate).

Figure 10:
FIG. 10 illustrates an expanded view of another display screen of the patient-application, as shown on a graphical user interface of the computing device, in accordance with some implementations of the current subject matter.

FIG. 10 illustrates an expanded view of the display screen 510. The display screen 510 displays the electrical activity in the form of the PQRST complex 1002 of the ECG 1004 of the patient 106. The display screen 510 can provide a button 1006, which, when selected by the user, can cause the patient-application 108 to save the ECG report in the one or more databases 414.

The P wave within the PQRST complex 1002 can correspond to the atrial depolarization and the pumping of blood from the atrium to the ventricle. Each QRS complex within the within the PQRST complex 1002 comes after a P wave for the atrium and ventricle to work synchronously. The QRS can correspond to the depolarization of blood and the pumping out of blood from the ventricle to the body and lung. There can be a short delay between the P wave and the QRS complex to allow time to fill the ventricle with blood and get ready to pump. The T wave within the PQRST complex 1002 can correspond to the repolarization of the ventricle and the recovery of the ventricle for the next cycle.

Figure 11:
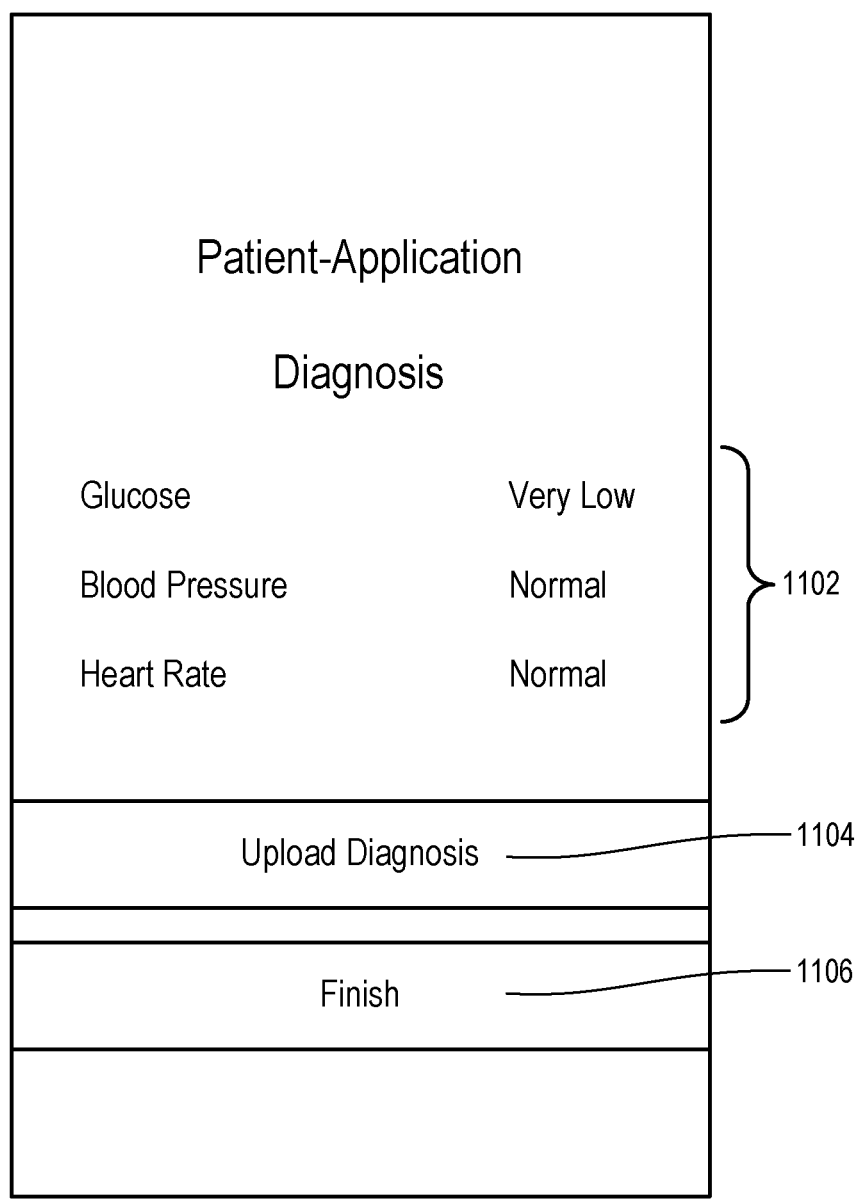
FIG. 11 illustrates an expanded view of another display screen of the patient-application, as shown on a graphical user interface of the computing device, in accordance with some implementations of the current subject matter.

FIG. 11 illustrates an expanded view of the display screen 512. The display screen 512 displays diagnosis 1102 of the physiological parameters (e.g., blood glucose, blood pressure and heart rate) based on the readings of those parameters monitored by the glove 102. The display screen 512 can provide a button 1104, which, when selected by the user, can cause the patient-application 108 to upload the diagnosis to a secured patient portal of a clinician or hospital. The display screen 512 can provide a button 1106, which, when selected by the user, can cause the patient-application 108 to complete the diagnosis review and render a display screen showing the home page of the patient-application.

Figure 12:
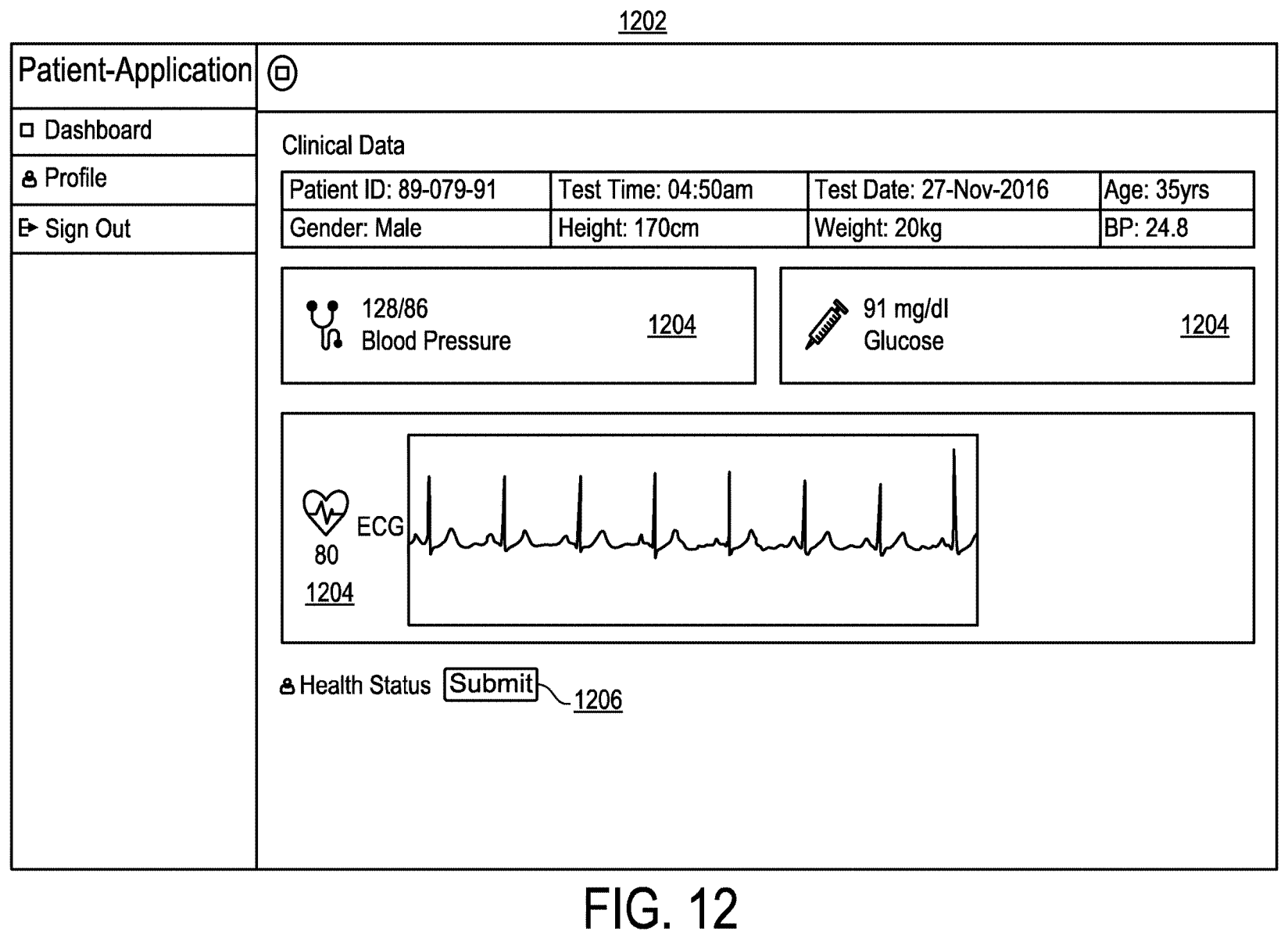

FIG. 12 illustrates a display screen 1202 rendered by the clinician-application 112. The display screen 1202 displays the clinical data for the patient 106, including the readings 1204 and/or corresponding displays for physiological parameters (e.g., blood pressure, blood glucose, oxygen saturation level, and/or electrical activity of the heart) of the patient 106. The display screen 1202 further displays a status of the health of the patient.

Figure 13:
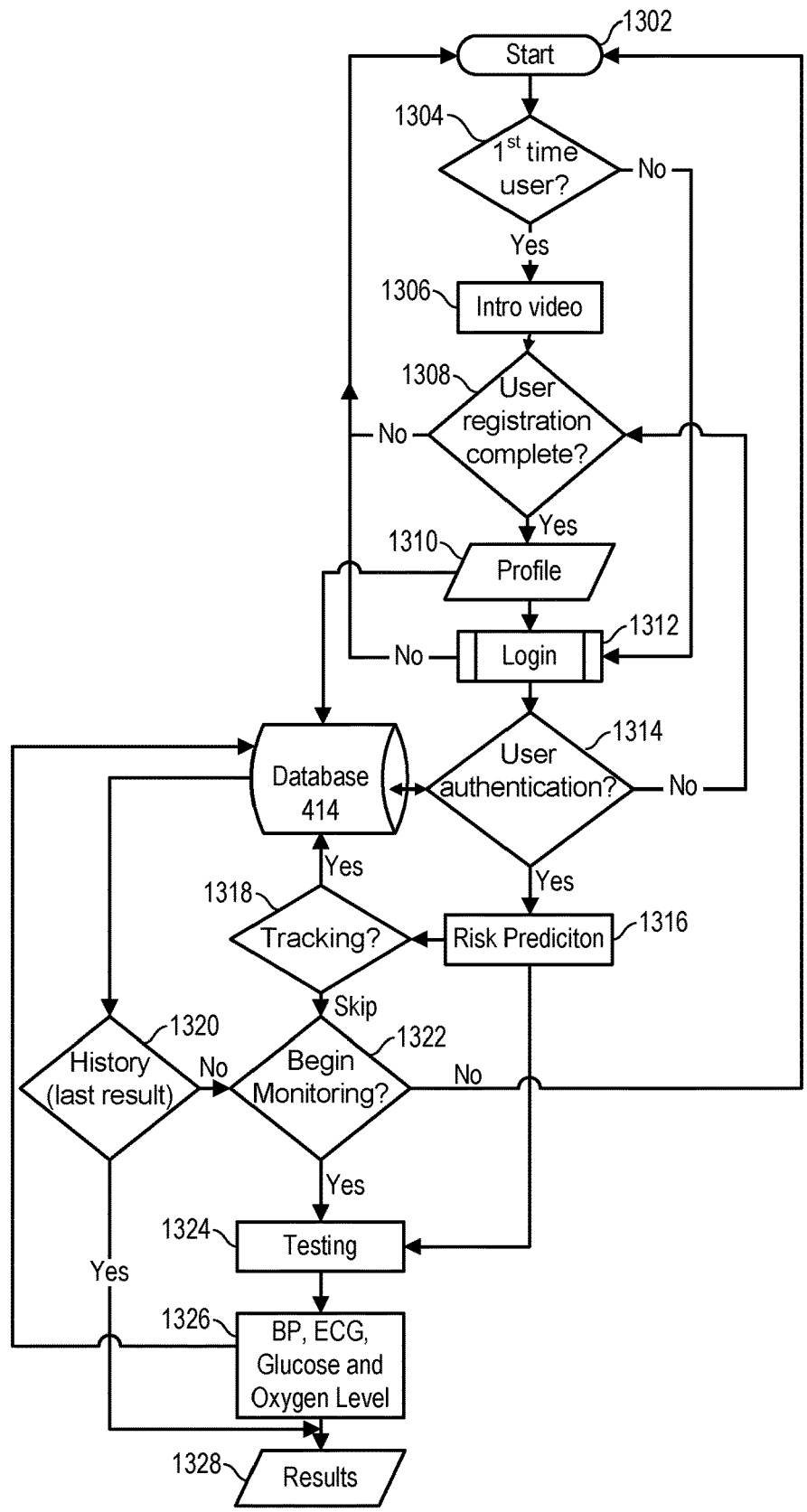
FIG. 13 illustrates a method of executing the patient-application, in accordance with some implementations of the current subject matter.

FIG. 13 illustrates a method of executing the patient-application 108. The one or more processors 412 can start, at 1302, the patient-application 108. The one or more processors 412 can determine, at 1304, whether the user is a first time user of the patient-application 108. The one or more processors 412 can make this determination by prompting the user to input, on a display screen, whether he or she is a first time user. If the user is a first-time user, the one or more processors 412 can render, at 1306, an introduction video explaining features and benefits of the patient-application 108 on a display screen of the computing device 104. The one or more processors 412 can render the display screen 502 on the patient-application 108 so that the user can register. The one or more processors 412 can determine, at 1308, whether the user has completed the registration. If the user has not completed the registration, the one or more processors 412 can render the home screen that allows the user to register. If the user is registered on the patient-application 108, the one or more processors 412 can create, at 1310, a profile for the user and store the file in the one or more databases 414.

The one or more processors 412 can display the display screen 504 so that the user can input, at 1312, the login information for accessing the patient-application 108. The one or more processors 412 can determine, at 1314, whether the login information is accurate to authenticate the user. If the user is not authenticated, the one or more processors 412 can determine, again at 1308, whether the user has completed the registration. If the user is authenticated, the one or more processors 412 can initiate, at 1316, the risk prediction module to predict the risk that the patient 106 has for abnormal values of physiological parameters (e.g., blood pressure, blood glucose, oxygen saturation level, and/or electrical activity of the heart). As a part of the risk prediction module 1316, the one or more processors 412 can determine, at 1318, whether the glove 102 has been tracking/monitoring physiological parameters in the past (e.g., continuously) on the patient 106. If the glove 102 has been tracking/monitoring physiological parameters in the past, the one or more processors 412 have saved the tracked clinical data in the one or more databases 414. The one or more processors can determine, at 1320, whether clinical data is available in the one or more databases 414.

If the clinical data is available in the one or more databases 414, the one or more processors 412 can display the diagnosis based on the monitored data on the display screens 510 and 512. If the clinical data is not available in the one or more databases 414, the one or more processors 412 can determine, at 1322, whether the monitoring of the physiological parameters (e.g., blood pressure, blood glucose, oxygen saturation level, and/or electrical activity of the heart) using the glove 102 can begin. The monitoring cannot begin in some instances, such as when the glove is not available or when the glove is not functional. If the monitoring of the physiological parameters can begin, the one or more processors 412 can display instructions to use the glove 102 so that the monitoring/testing of the physiological parameters can begin at 1324. The one or more processor 412 can generate, at 1326, a display of readings of the physiological parameters. The one or more processor 412 can generate, at 1328, a diagnosis based on the readings of the physiological parameters. The one or more processor 412 can display the generated diagnosis on display screens 512 and/or 1202.

Figure 14:
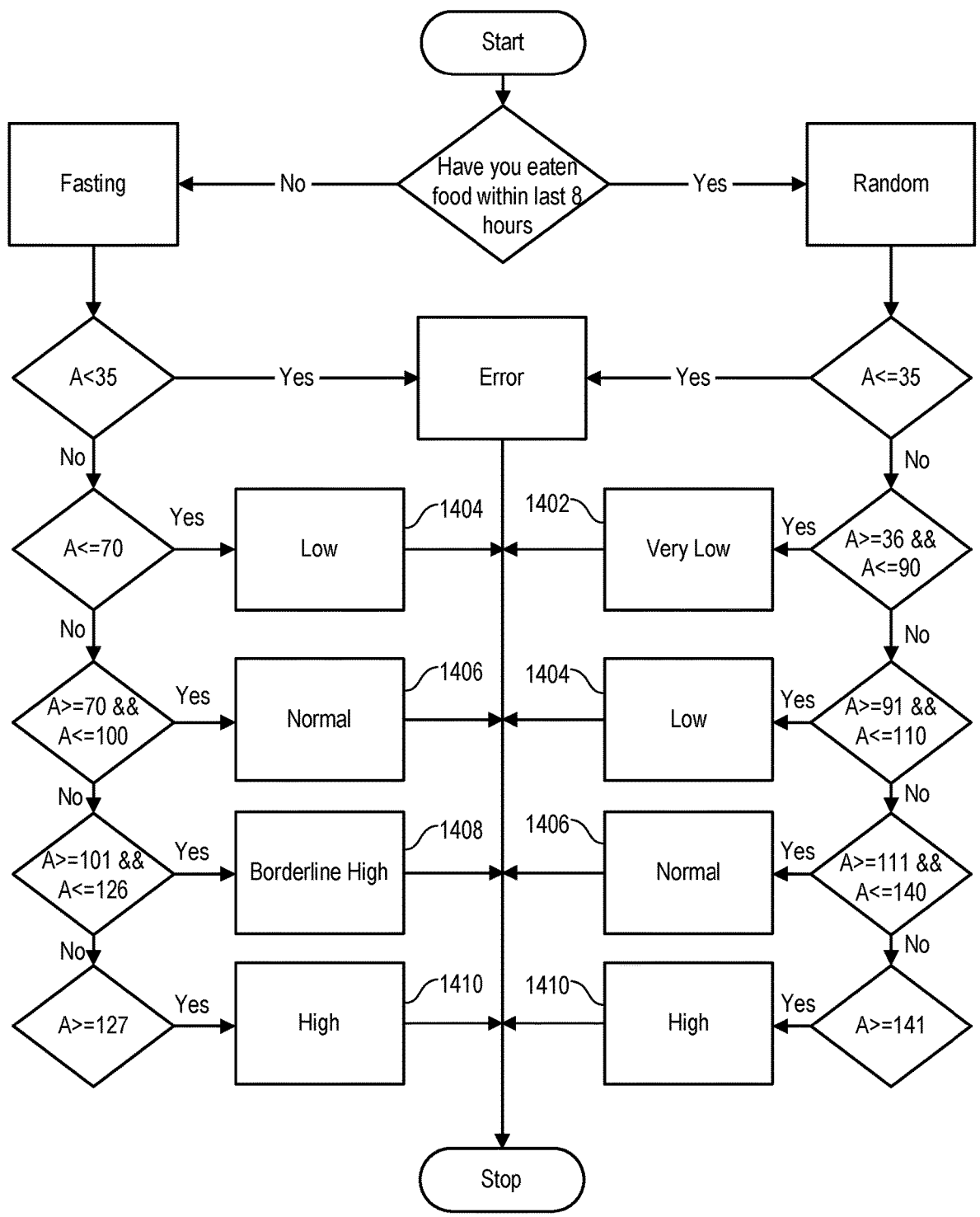
FIG. 14 illustrates a process performed, by either the patient-application or the computing server, for identifying a physiological condition—e.g., very low sugar level, low sugar level, normal sugar level, borderline high sugar level, or high sugar level—of a patient based on: (a) readings of average blood glucose level, (b) whether the patient is fasting, in accordance with some implementations of the current subject matter.

FIG. 14 illustrates a process performed, by either the patient-application 108 in one implementation or the computing server 110 in another implementation, for identifying a physiological condition—e.g., very low sugar level 1402, low sugar level 1404, normal sugar level 1406, borderline high sugar level 1408, or high sugar level 1410—of a patient 106 based on: (a) readings taken by the glove 102 of a physiological parameter, such as average blood glucose level "A," and (b) whether the patient 106 has eaten within the past preset amount of time such as eight hours (i.e., whether the patient 106 is fasting). The average blood glucose level can be average of glucose levels measured over a period of time, such as two to three months.

The values of average blood glucose are presented in milligrams per deciliter in the drawing. The low sugar level 1404 can be associated with a glucose level cutoff at 70 milligrams per deciliter, which is different from 90 milligrams per deciliter value traditionally proposed by clinicians. Such difference in value is advantageous because it accounts for potential errors caused due to the non-invasive nature of the glove 102, thereby resulting in a precautionary diagnosis to ensure patient safety. Similarly, other numeric values associated with other physiological conditions 1402, 1406, 1408 and 1410 have been adjusted from the corresponding values traditionally proposed by clinicians to warrant such precautions to ensure patient safety. In some implementations, each of one or more (e.g., all) numeric blood sugar values shown in the drawing can be replaced with another value that is plus-minus five of the shown numeric value.

Figure 15:
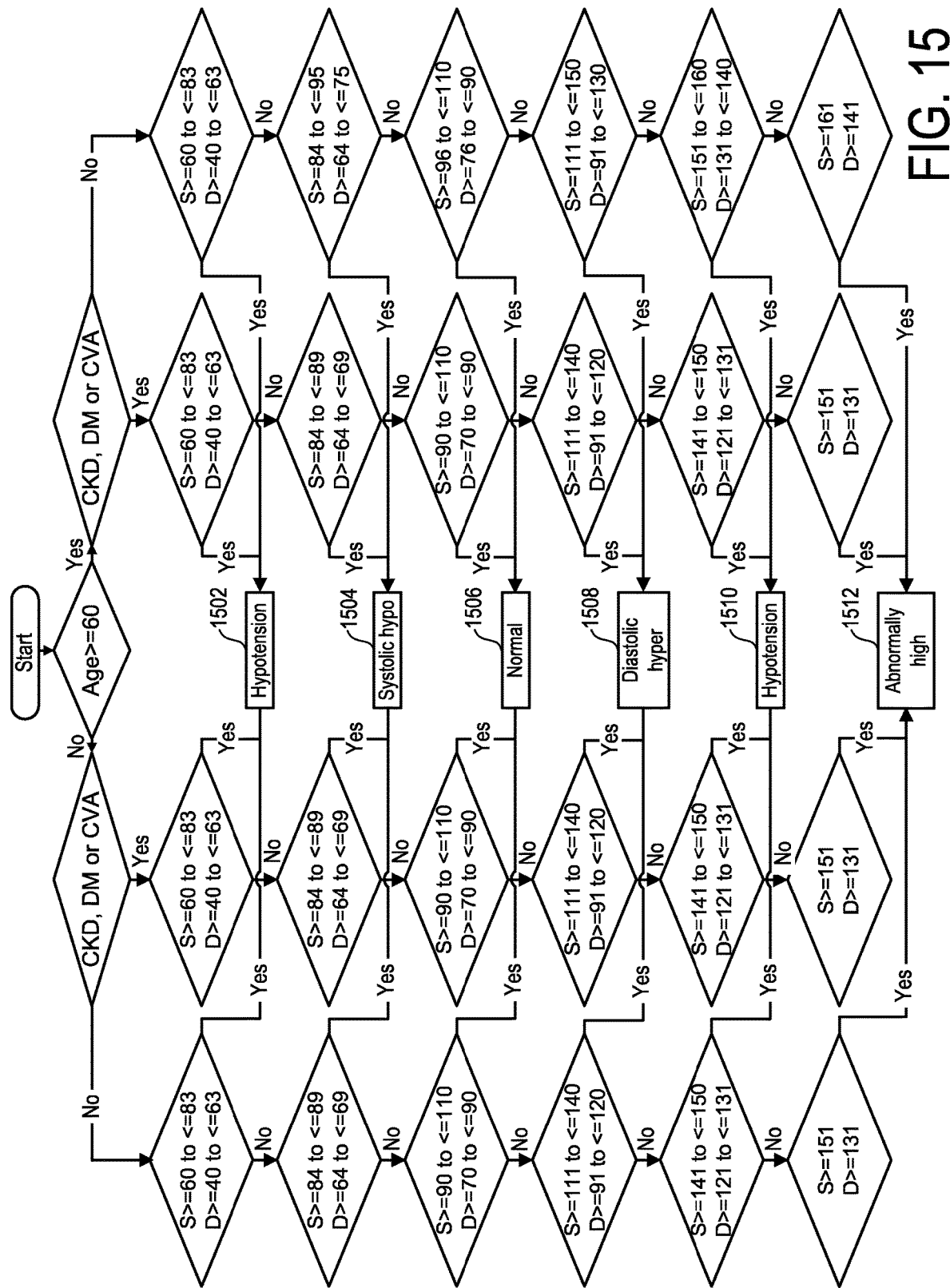
FIG. 15 illustrates a process performed, by either the patient-application or the computing server, for identifying a physiological condition—e.g., hypotension, systolic hypotension, normal blood pressure, diastolic hypertension, hypertension, or very/abnormally high blood pressure—of a patient based on: (a) readings of physiological parameters, such as systolic blood pressure and diastolic blood pressure, (b) age of the patient, and (c) whether the patient currently has or has had one or more of a chronic kidney disease (CKD), diabetes mellitus (DM), or cerebra vascular accident (CVA; also referred to as stroke), in accordance with some implementations of the current subject matter.

FIG. 15 illustrates a process performed, by either the patient-application 108 in one implementation or the computing server 110 in another implementation, for identifying a physiological condition—e.g., hypotension 1502, systolic hypotension 1504, normal blood pressure 1506, diastolic hypertension 1508, hypertension 1510, or very/abnormally high blood pressure 1512—of a patient 106 based on: (a) readings taken by the glove 102 of physiological parameters, such as systolic blood pressure "S" and diastolic blood pressure "D," (b) age of the patient 106, and (c) whether the patient currently has or has had one or more of a chronic kidney disease (CKD), diabetes mellitus (DM), or cerebra vascular accident (CVA; also referred to as stroke).

Differentiating between systolic and diastolic blood pressure is important for clinically determining the therapy that should be provided to the patient 106. The values of blood pressure are presented in millimeters of mercury in the drawing. The blood pressure values shown in the drawing are those that maximize accuracy of the diagnosis and precaution. In alternate implementations, each of one or more (e.g., all) numeric blood pressure values shown in the drawing can be replaced with another value that is plus-minus five of the shown numeric value so as to ensure accuracy of diagnosis, precaution and patient safety.

Figure 16:
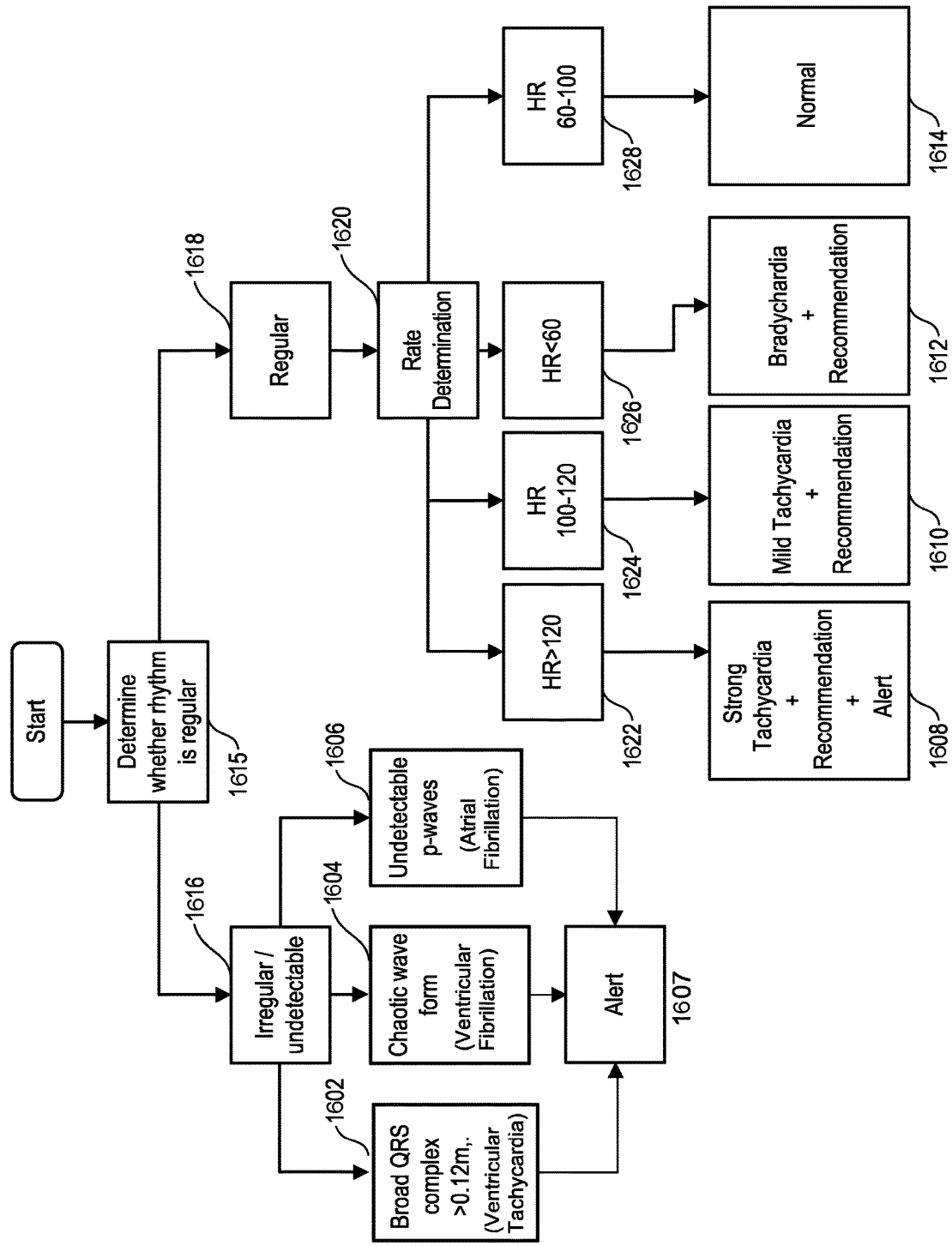
FIG. 16 illustrates a process performed, by either the patient-application or the computing server, for identifying a physiological condition—e.g., broad QRS complex, chaotic waveform, undetectable P-waves, a strong form of tachycardia, a mild form of tachycardia, bradycardia, or normal heart rate—of a patient based on programmed analysis of the cardiac rhythm of the patient as monitored by the glove, in accordance with some implementations of the current subject matter.

FIG. 16 illustrates a process performed, by either the patient-application 108 in one implementation or the computing server 110 in another implementation, for identifying a physiological condition—e.g., broad QRS complex 1602, chaotic waveform 1604, undetectable P-waves 1606, a strong form of tachycardia 1608, a mild form of tachycardia 1610, bradycardia 1612, or normal heart rate 1614—of a patient 106 based on programmed analysis of the cardiac rhythm monitored by the glove 102 at 1615. To execute the programmed analysis, the computing server 110 can first determine regularity, or irregularity, in the cardiac rhythm, which can be detected by determining the periodicity of the P wave.

If the rhythm is determined to be irregular at 1616, the patient-application 108 or the computing server 110 can analyze whether: (a) the QRS complex of the patient 106 is broad, which indicates ventricular tachycardia (at 1602), (b) the QRS complex of the patient 106 is chaotic, which indicates ventricular fibrillation (at 1604), and/or (c) the patient 106 has a stroke prone rhythm where the QRS is irregular with no detectable P waves, which indicates atrial fibrillation (at 1606). If the QRS complex is broad or chaotic, or if there are no detectable P waves, the patient-application 108 or the computing server 110 can generate/ facilitate an alert (at 1607). The generated alert can be produced on the one or more of the glove 102, the patient-application 108 and the clinician-application 112. The alert can be a sound alert, a light alert such as a flashing light or constantly activated light, or the like. In some implementations, the alert can be accompanied by a text message, email, social network message, phone call, and/or the like to the patient 106.

If the rhythm is determined to be regular at 1618 (i.e., regular rhythm with P waves present/detected, and properly formed QRS complexes), the patient-application 108 or the computing server 110 can determine the heart rate at 1620. The patient-application 108 or the computing server 110 can analyze the determined heart rate based on physiologic or pathologic responses.

If the determined heart rate (also referred to as HR in the drawing) is more than one hundred and twenty beats per minute (at 1622), the heart rate is considered very high, and this condition is referred to as a strong form of tachycardia 1608. In such case, the patient-application 108 or the computing server 110 can generate and display, on a graphic user interface: (a) an explanation describing the following related to the strong form of tachycardia: physiological description, pathological description, symptoms, potential causes, risk factors, possible complications, ways of prevention, treatment options, and (b) a recommendation that the patient 106 should go see a clinician. In addition, the patient-application 108 or the computing server 110 can also generate an alert. This alert can be produced on the one or more of the glove 102, the patient-application 108 and the clinician-application 112. The alert can be a sound alert, a light alert such as a flashing light or constantly activated light, or the like. In some implementations, the alert can be accompanied by a text message, email, social network message, phone call, and/or the like to the patient 106.

If the determined heart rate is more than one hundred beats per minute (at 1624), the heart rate is considered high, and this condition is referred to as a mild form of tachycardia 1610. In such case, the patient-application 108 or the computing server 110 can generate and display, on a graphic user interface: (a) an explanation describing the following related to the mild form of tachycardia: physiological description, pathological description, symptoms, potential causes, risk factors, possible complications, ways of prevention, treatment options, and (b) a recommendation that the patient 106 should go see a clinician.

If the determined heart rate is less than sixty beats per minute (at 1626), the heart rate is considered low, and this condition is referred to as bradycardia 1612. The patient-application 108 or the computing server 110 can generate and display, on a graphic user interface: (a) an explanation describing the following related to bradycardia: physiological description, pathological description, symptoms, potential causes, risk factors, possible complications, ways of prevention, treatment options, and (b) a recommendation that the patient 106 should go see a clinician.

If the determined heart rate is between sixty and one hundred beats per minute (at 1628), the heart rate is considered normal 1614. In this case, the patient-application 108 or the computing server 110 can generate and display, on a graphic user interface, an explanation describing the physiological and pathological activities related to the normal heart rate.

Various implementations of the subject matter described herein can be realized/implemented in digital electronic circuitry, integrated circuitry, specially designed application specific integrated circuits (ASICs), computer hardware, firmware, software, and/or combinations thereof. These various implementations can be implemented in one or more computer programs. These computer programs can be executable and/or interpreted on a programmable system. The programmable system can include at least one programmable processor, which can have a special purpose or a general purpose. The at least one programmable processor can be coupled to a storage system, at least one input device, and at least one output device. The at least one programmable processor can receive data and instructions from, and can transmit data and instructions to, the storage system, the at least one input device, and the at least one output device.

These computer programs (also known as programs, software, software applications or code) can include machine instructions for a programmable processor, and can be implemented in a high-level procedural and/or object-oriented programming language, and/or in assembly/machine language. As can be used herein, the term "machine-readable medium" can refer to any computer program product, apparatus and/or device (for example, magnetic discs, optical disks, memory, programmable logic devices (PLDs)) used to provide machine instructions and/or data to a programmable processor, including a machine-readable medium that can receive machine instructions as a machine-readable signal. The term "machine-readable signal" can refer to any signal used to provide machine instructions and/or data to a programmable processor.

The computing server described herein can, in some implementations, make predictions of the physiological conditions using a predictive model. The predictive model can be a regression based model or a machine-learning based model. The regression model can be one of: a linear regression model, a discrete choice model, a logistic regression, a multinomial logistic regression, a probit regression, a logit regression, a time-series model, a survival or duration model, a classification and regression tree (CART), multivariate adaptive regression splines, any other regression model, any combination thereof, and/or the like. The machine-learning based model can be: a neural network, a multilayer perceptron (MLP), a radial basis function, a support vector machine, a Naïve Bayes model, k-nearest neighbors model, a geospatial predictive model, any other machine-learning based model, any combination thereof, and/or the like.

To provide for interaction with a user, the subject matter described herein can be implemented on a computer that can display data to one or more users on a display device, such as a light emitting diode (LED) monitor, a cathode ray tube (CRT) device, a liquid crystal display (LCD) monitor, an electroluminescent display (ELD) device, a plasma display panel (PDP), an organic light-emitting diode display (OLED) device, or any other display device. The computer can receive data from the one or more users via a keyboard, a mouse, a trackball, a joystick, or any other input device. To provide for interaction with the user, other devices can also be provided, such as devices operating based on user feedback, which can include sensory feedback, such as visual feedback, auditory feedback, tactile feedback, and any other feedback. The input from the user can be received in any form, such as acoustic input, speech input, tactile input, or any other input.

The subject matter described herein can be implemented in a computing system that can include at least one of a back-end component, a middleware component, a front-end component, and one or more combinations thereof. The back-end component can be a data server. The middleware component can be an application server. The front-end component can be a client computer having a graphical user interface or a web browser, through which a user can interact with an implementation of the subject matter described herein. The components of the system can be interconnected by any form or medium of digital data communication, such as a communication network. Examples of communication networks can include a local area network, a wide area network, internet, intranet, BLUETOOTH network, infrared network, or other networks.

Although a few variations have been described in detail above, other modifications can be possible. For example, the logic flows depicted in the accompanying figures and described herein do not require the particular order shown, or sequential order, to achieve desirable results. Additional implementations may be within the scope of the following claims.

What is claimed is:

1. A glove comprising:
first sensor configured to be placed around an index finger of a patient and to monitor blood glucose of the patient;
electrocardiograph connectors disposed at a portion of the glove corresponding to a wrist of the patient and configured to monitor electrical activity of a heart of the patient;
a cuff configured to use a pressure sensor monitor to measure a systolic blood pressure and a diastolic blood pressure of the patient, monitoring of the blood glucose, the electrical activity of the heart, the systolic blood pressure, and the diastolic blood pressure occurring simultaneously; and
a processor communicatively coupled to a computing server executing a machine-learning model configured to predict a diagnosis of physiological conditions based on the blood glucose, the electrical activity, the systolic blood pressure, and the diastolic blood pressure all together.

2. The glove of claim 1, wherein the blood glucose, the electrical activity, the systolic blood pressure, and the diastolic blood pressure are monitored non-invasively,
wherein the glove further comprises a display device configured to display data associated with one or more of the blood glucose, the electrical activity of the heart, the systolic blood pressure, and the diastolic blood pressure, wherein the display device is attached to the cuff,
wherein the first sensor, the electrocardiograph connectors, the cuff, and the display device are a part of the glove, and
wherein the first sensor comprises an infrared sensor.

3. The glove of claim 1, wherein each physiological condition indicates a level of a plurality of levels associated with the physiological condition, and
wherein the machine-learning model comprises one or more of a neural network model, a multilayer perceptron, a radial basis function, a support vector machine, a Naïve Bayes model, k-nearest neighbors model, or a geospatial predictive model.

4. The glove of claim 3, wherein the processor and the computing server are communicatively coupled to a communication device that executes a first application configured to generate the diagnosis of physiological conditions based on the blood glucose, the electrical activity, the systolic blood pressure, and the diastolic blood pressure together.

5. The glove of claim 4, wherein, in response to receipt of authentication data uniquely identifying the patient, the first application is configured to display the diagnosis of the physiological conditions on a graphical user interface of the communication device, and wherein the first application is configured to display digital content and to upload data comprising the diagnosis of the physiological conditions to a secure database configured to store diagnostic data in response to a selection of the digital content.

6. The glove of claim 3, wherein the physiological conditions comprise:
hypotension or hypertension,
hypoglycemia or hyperglycemia,
hypoxia or hyperoxia, and
arrhythmia.

7. The glove of claim 1, wherein the electrocardiograph connectors are three electrocardiograph connectors.

8. The glove of claim 1, wherein the first sensor is configured to detect the blood glucose over a period of time that exceeds one month.

9. A system comprising:
a glove configured to monitor values of physiological parameters associated with a patient simultaneously and non-invasively, and to display data associated with the values of the physiological parameters on a display device located on the glove; and
a computing device configured to execute an application to:
receive, via a first communication network, the data associated with the values of the physiological parameters;
receive input patient data associated with a patient profile;
apply a machine-learning model that is configured to generate a diagnosis of one or more physiological conditions of the patient based on the data associated with the values of the physiological parameters and the input patient data, the physiological parameters comprising blood pressure, blood glucose, oxygen saturation level, and electrical activity of a heart of the patient all together; and
display the diagnosis on a display screen of the application.

10. The system of claim 9, wherein:
the at least one machine-learning model comprises one or more of a linear regression model, a discrete choice model, a logistic regression, a multinomial logistic regression, a probit regression, a logit regression, a time-series model, a survival or duration model, a classification and regression tree, or multivariate adaptive regression splines; and
the one or more physiological conditions comprise one or more of hypotension, hypertension, hypoglycemia, hyperglycemia, hypoxia, hyperoxia, and arrhythmia.

11. The system of claim 10, wherein generation of the diagnosis comprises generating a PQRST complex based on the electrical activity of the heart.

12. The system of claim 10, wherein generation of the diagnosis comprises averaging the blood pressure over a preset period of time that is at least two months, and wherein the computing device comprises a mobile phone.

13. The system of claim 9, wherein the first communication network is a network other than an infrared network, wherein the application is further configured to communicate with a computing server via a second communication network to create a database of clinical data of the patient, the database being a part of the computing server.

14. The system of claim 13, wherein the computing server is a cloud computing server, wherein the cloud computing server comprises at least one normalization processor communicatively coupled to the glove, at least one software development kit communicatively coupled to the application, and at least one web module communicatively coupled to the computing device, wherein the normalization processor, the at least one normalization processor, the at least one software development kit, and the at least one web module are coupled to an application programming interface implemented on the cloud computing server.

15. A method comprising:
simultaneously acquiring, by a glove worn by a patient, data associated with the physiological parameters from a patient;
displaying, on a display device located on the glove, the data associated with the physiological parameters; and
transmitting, by a transmitter of the glove and via a communication network, the data associated with the physiological parameters to an application executed on a computing device,
wherein the application is configured to utilize a machine-learning model to estimate one or more physiological conditions determined based on the data associated with physiological parameters comprising blood pressure, blood glucose, oxygen saturation level, electrical activity of a heart, and heart rate of the patient all together.

16. The method of claim 15, wherein the application is configured to display the one or more physiological conditions, wherein the one or more physiological conditions comprise hypotension or hypertension, hypoglycemia or hyperglycemia, hypoxia or hyperoxia, and arrhythmia.

17. The glove of claim 1, comprising:
a first connector of the electrocardiograph connectors is located in a portion of the glove corresponding to a thumb of the patient.

18. The glove of claim 17, comprising:
a second connector of the electrocardiograph connectors connected to the first connector through a device case attached to a cuff and a display.

19. The glove of claim 1, wherein the glove comprises:
an air pump configured to pump air onto a hand of the patient within the glove; and
an electromechanical device configured to control a generation of magnetic fields to facilitate functioning of the air pump.

* * * * *